United States Patent
Hong et al.

(10) Patent No.: US 9,782,166 B2
(45) Date of Patent: Oct. 10, 2017

(54) SUTURING BEAD, SUTURING NEEDLE, SIDE SUCTION CAP AND ENDOSCOPIC ORGAN SUTURING IMPLEMENT USING SAME

(71) Applicant: Korea University Research and Business Foundation, Seoul (KR)

(72) Inventors: Dae Hie Hong, Anyang-si (KR); Byung Gon Kim, Seoul (KR); Kyoung Nam Kim, Seoul (KR); Yoon Jin Kim, Seoul (KR); Hoon Jai Chun, Seoul (KR); Bo Ra Keum, Seoul (KR); Hyuk Soon Choi, Seoul (KR)

(73) Assignee: Korea University Research And Business Foundation, Seoul (KR)

( * ) Notice: Subject to any disclaimer, the term of this patent is extended or adjusted under 35 U.S.C. 154(b) by 149 days.

(21) Appl. No.: 14/396,175

(22) PCT Filed: Nov. 21, 2012

(86) PCT No.: PCT/KR2012/009882
§ 371 (c)(1),
(2) Date: Oct. 22, 2014

(87) PCT Pub. No.: WO2013/162143
PCT Pub. Date: Oct. 31, 2013

(65) Prior Publication Data
US 2015/0127023 A1 May 7, 2015

(30) Foreign Application Priority Data
Apr. 27, 2012 (KR) ........................ 10-2012-0044913

(51) Int. Cl.
*A61B 17/04* (2006.01)
*A61B 17/06* (2006.01)
(Continued)

(52) U.S. Cl.
CPC ...... *A61B 17/0482* (2013.01); *A61B 17/0401* (2013.01); *A61B 17/0469* (2013.01);
(Continued)

(58) Field of Classification Search
None
See application file for complete search history.

(56) References Cited

U.S. PATENT DOCUMENTS 5,203,787 A * 4/1993 Noblitt ............... A61B 17/0401
411/460
2003/0191369 A1 * 10/2003 Arai .................. A61B 1/00101
600/173
(Continued)

FOREIGN PATENT DOCUMENTS

JP 2004-601 A 1/2004
JP 2008-206973 A 9/2008
(Continued)

OTHER PUBLICATIONS

International Search Report issued Feb. 22, 2013 in counterpart National Stage Application No. PCT/KR2012/009882 (4 pages, in Korean, with English language translation).

*Primary Examiner* — Shaun L David
(74) *Attorney, Agent, or Firm* — NSIP Law (57) ABSTRACT

The present invention relates to a suturing bead, a suturing needle, a side suction cap and to an endoscopic organ suturing implement using same. More specifically, the present invention relates to an endoscopic organ suturing implement comprising a suturing bead which can be naturally rested lying against the organ wall during discharge, a suturing needle by means of which it is possible to control discharge of the suturing bead, and a side suction cap constituted in such a way as to be able to prevent damage to other organs during surgery.

3 Claims, 6 Drawing Sheets

(51) Int. Cl.
*A61B 17/30* (2006.01)
*A61B 17/00* (2006.01)

(52) U.S. Cl.
CPC  *A61B 17/06166* (2013.01); *A61B 2017/0034* (2013.01); *A61B 2017/00296* (2013.01); *A61B 2017/047* (2013.01); *A61B 2017/0409* (2013.01); *A61B 2017/0417* (2013.01); *A61B 2017/0474* (2013.01); *A61B 2017/0475* (2013.01); *A61B 2017/06052* (2013.01); *A61B 2017/06176* (2013.01); *A61B 2017/306* (2013.01)

(56) References Cited

U.S. PATENT DOCUMENTS

| | | | | |
|---|---|---|---|---|
| 2005/0033363 | A1* | 2/2005 | Bojarski | A61B 17/0401 606/228 |
| 2006/0276692 | A1* | 12/2006 | Kucklick | A61B 1/00135 600/175 |
| 2007/0073342 | A1* | 3/2007 | Stone | A61B 17/0057 606/232 |
| 2008/0208220 | A1* | 8/2008 | Shiono | A61B 17/0401 606/144 |
| 2010/0004665 | A1* | 1/2010 | Hong | A61B 17/0401 606/148 |
| 2010/0145385 | A1* | 6/2010 | Surti | A61B 17/0401 606/232 |
| 2010/0238279 | A1* | 9/2010 | Thoms | A61B 1/00089 348/77 |
| 2013/0046331 | A1* | 2/2013 | Christensen | A61B 17/12 606/200 |
| 2013/0317295 | A1* | 11/2013 | Morse | A61B 1/00165 600/109 |

FOREIGN PATENT DOCUMENTS

| | | |
|---|---|---|
| KR | 10-2006-0009698 A | 2/2006 |
| KR | 10-0838983 B1 | 6/2008 |

\* cited by examiner

SUTURING BEAD, SUTURING NEEDLE, SIDE SUCTION CAP AND ENDOSCOPIC ORGAN SUTURING IMPLEMENT USING SAME

TECHNICAL FIELD

The invention relates to a suturing bead, a suturing needle, a side suction cap and to an endoscopic organ suturing implement using same and in particular to a an endoscopic organ suturing implement comprising a suturing bead which can be naturally rested lying against the organ wall during discharge, a suturing needle by means of which it is possible to control discharge of the suturing bead and a side suction cap constituted in such a way as to be able to prevent damage to other organs during surgery.

BACKGROUND ART

An endoscope tube is an apparatus to examine lesion directly by inserting an instrument into the organ which cannot be examined without surgery or autopsy. As an endoscope tube, there are various types such as an endoscope tube having one tube to look the organ directly, an endoscope tube using a lens system, an endoscope tube having a camera inserted into the organ directly, a fiberscope using glass fiber, etc.

Recently, various surgery devices are developed by which medical operation is possible on the interior of an organ without an incision of a body by attaching a suturing device to the endoscope tube and then inserting it into the body. "Suturing bead, Vacuum cap for organ suction and Organ suturing device using the same" (Korean patent No. 10-0838983) owned by the applicant of the present invention was registered.

Prior suturing bead has problems in that it has a large friction surface with respect to a suture and it has a difficulty in moving through a suturing needle, thereby a plurality of beads being discharged for one stitch.

Also, in case of prior suturing needle, there is no way to check whether the suturing bead is discharged properly, which results in the waste of suturing beads and the difficulty of operation.

Further, prior vacuum cap has a problem in that it cannot check whether the suturing needle penetrates the sucked organ and whether the suturing bead is discharged properly.

DISCLOSURE OF THE INVENTION

Technical Problem

The present invention is invented to solve the above problems and the object of the invention is to provide a suturing bead which penetrates an organ and does not return to the interior of the organ.

The object is also to provide a suturing needle which prevents the waste of the suturing bead by controlling the discharge of the suturing bead and facilitate the surgery.

Another object of the present invention is to provide a side suction cap by which observation is feasible on the surgery area and it is possible to check whether the suturing bead is discharged for the proper suturing and an endoscopic organ suturing implement using the same.

Technical Solution

To achieve the object, the invention provides a suturing bead comprising: a body having an arc-shaped cross section; and a suture-penetrating part which protrudes from one side of the body and through which a suture passes.

Also, the suturing-penetrating part is formed such that it is inclined along the length of the bead from one side of the body to the other side.

Also, a suturing needle which discharges a suturing bead comprising: a bead stopper by which the discharge of the suturing bead is controlled at the discharge opening of the suturing needle; and a dummy bead which makes it possible to check whether the suturing bead is discharged.

Also, a side suction cap which engages with the end of an endoscope tube having a suction tube and sucks a portion of an organ comprising: a coupling part which engages with the end of the endoscope tube; a suction port which introduces the organ into the side suction cap crossingly to the direction of the engagement of the endoscope tube with the side suction cap; a push-preventing member which is disposed on the side opposite to the coupling part, and is installed at the end of the suction port to provide support in such a manner that the organ is not pushed; and a mirror part which is disposed diagonally on the side wall opposite to the coupling part.

Also, the suction port is arranged perpendicularly to the direction of the engagement of the endoscope tube with the side suction cap.

Also, the mirror part is configured to check the status of the suturing bead which is discharged from the suturing needle.

Also, an endoscopic organ suturing implement comprises: a suturing needle from which a suturing bead is discharged; an endoscope tube which has the suturing needle inside; and a side suction cap which has a coupling part with which the endoscope tube engages at one side thereof; a suction port which is formed crossingly to the direction of the engagement of the coupling part with the side suction cap; a push-preventing member which is disposed on the side opposite to the coupling part and is installed at the end of the suction port to provide support in such a manner that an organ is not pushed; and a mirror part which is disposed diagonally on the side wall opposite to the coupling part.

Also, the suturing needle further comprises a bead stopper by which the discharge of the suturing bead is controlled at the discharging opening; and a dummy bead which makes it possible to check whether the suturing bead is discharged.

Also, the suction port is arranged perpendicularly to the direction of the engagement of the endoscope tube with the side suction cap.

Further, the mirror part is configured to check the status of the suturing bead which is discharged from the suturing needle.

Advantageous Effect

The suturing bead according to the present invention is controlled easily since friction surface with a suture is small compared to the prior art. Also, the suturing bead according to the present invention is longer than the prior suturing bead, resulting in the prevention of the waste of the suturing bead, the convenience of surgery and the reduction of surgery time.

Also, the suturing needle of prior art cannot prevent the suturing bead from returning to the suturing needle after the bead was discharged and it is impossible to check whether the suturing bead is discharged properly. However, this problem is solved by a bead stopper and a dummy bead according to the present invention, thereby simpler and more accurate surgery being achieved.

Also, the use of the side suction cap according to the present invention makes it possible to observe the area opposite to the organ in order to check whether the suturing bead is discharged properly and rests on the organ. Therefore, more accurate surgery can be obtained.

Also, since the endoscopic organ suturing implement of the present invention can suture both mucous layer and panniculus carnosus, the recovery period of the patient can be shortened. Further, the suturing can be made enough with one insertion of the suturing implement, thereby reducing the surgery time and fatigability of surgeon remarkably.

MODE FOR CARRYING OUT THE INVENTION

Hereinafter, preferred embodiments of a suturing bead, a suturing needle, a side suction cap and to an endoscopic organ suturing implement using same according to the present invention will be explained in detail referring to attached drawings. Regarding reference numerals, it should be understood that the same constitutional elements have the same reference numeral even when they are provided in other drawings. Also, detailed descriptions of well-known constructions or their related function may be omitted for increased clarity and conciseness when they are believed to make the present invention vague.

Figure 1:
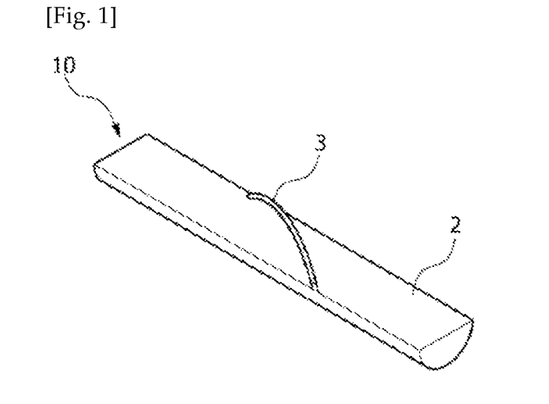
FIG. 1 is a perspective view of a suturing bead according to the present invention.

FIG. 1 is a perspective view of a suturing bead according to the present invention.

As shown in FIG. 1, the suturing bead 10 according to the present invention comprises a body 2 whose cross section is in the shape of an arc and a suture-penetrating part 3 which protrudes from one side and through which a suture (stitching fiber) 1 can pass. The suture-penetrating part 3 is formed such that it is inclined along the length of the bead from one side of the body 2 to the other side.

Figure 2:
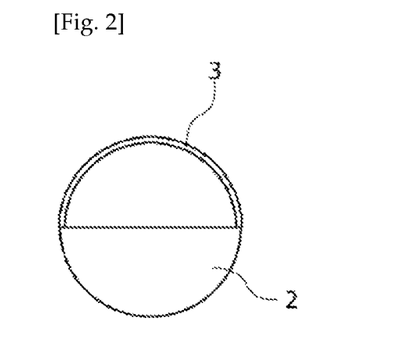
FIG. 2 is a cross-sectional view of a suturing bead according to the present invention.

FIG. 2 is a cross-sectional view of a suturing bead 10 according to the present invention and shows that the body 2 has an arc-shaped cross section and the suture-penetrating part 3 through which a suture 1 passes protrudes from one side and that the body and the suture-penetrating part are constituted to have a cross section of a circular shape. The material for the suturing bead 10 will be harmless to humans and there should not be any reaction to enzyme. Metal having no harm to humans such as Titanium will be preferred. Alternatively, it is preferable to make the suturing bead 10 with material which will dissolve and disappear easily. Further, the suture-penetrating part 3 may be constituted of a thin wire to minimize the friction between the suture 1 and the suture-penetrating part 3.

Figure 3:
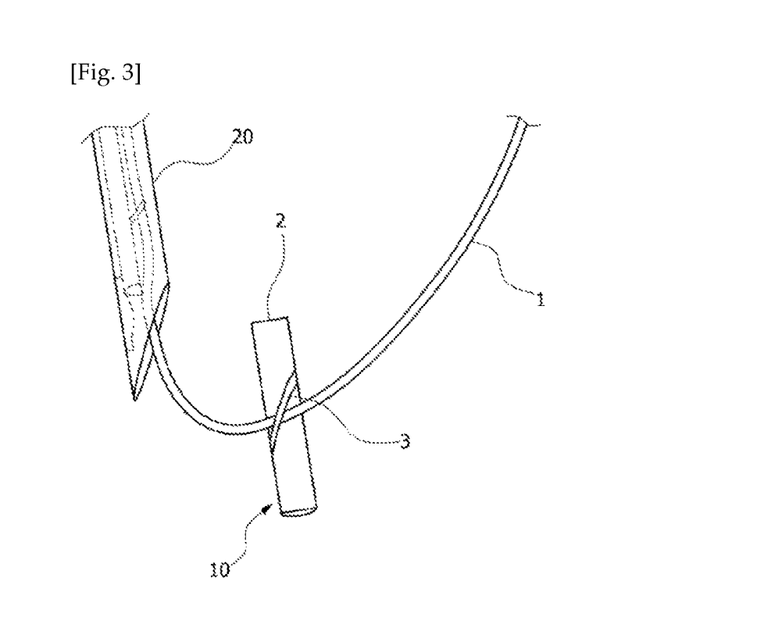
FIG. 3 shows that a suturing bead is fixed to the bottom of the organ by discharging it from a suturing needle and then by pulling a suture.

FIG. 3 shows that a suturing bead is fixed to the bottom of the organ when it is discharged from the suturing needle and then a suture is pulled out.

The suturing bead 10 is constituted to ensure the free movement relative to the suture 1 when it is located in the suturing needle 20 and to make the suturing bead 10 lie without any control when it is discharged from the suturing needle 20. That is, when the suture 1 is pulled out, the inclined suture-penetrating part 3 makes the suturing bead 10 rotate in a perpendicular direction so that it is fixed to the bottom of the organ. Since the prior-art suturing bead has a short length, it is not fixed to the bottom of the organ well when it rotated perpendicularly. However, the present invention solved the problem of the prior art by increasing the length of the suturing bead 10 and by reducing the friction with the suture 1. The suturing bead 10 is elongated in a manner that its length is longer than its breadth. The present invention makes it possible to fix one stitch by one suturing bead 10 while several suturing beads are required to fix one stitch in the prior-art.

Figure 4:
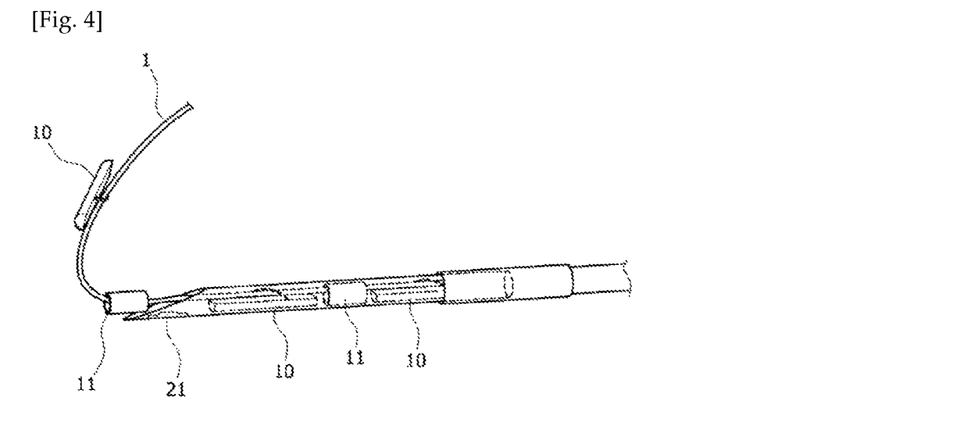
FIG. 4 is a perspective view of a suturing needle according to the present invention.

FIG. 4 is a perspective view of the suturing needle 20 according to the present invention and the suturing needle 20 comprises a bead stopper 21 by which the discharge of the suturing bead 10 is controlled at a discharge opening and a dummy bead 11 by which it can be checked whether the suturing bead 10 is discharged.

The suturing needle 20 has a bead stopper 21 to prevent the suturing bead 10 from sliding out of the suturing needle 20 regardless of the control of surgeon and to prevent the discharged suturing bead 10 from coming back into the suturing needle 20.

The dummy bead 11 is located between the suturing beads 10 and has no relation to the suturing. However, when a field of vision in the opposite to the organ is restricted and it is difficult to see if the suturing bead is discharged or not, the dummy bead 11 makes it possible to determine whether the suturing bead 10 is discharged. The dummy bead 11 has a cylindrical shape and is shorter than the suturing bead 10.

In the prior art, a plurality of suturing beads 10 are discharged for one stitch since there is no stopper 21. This problem is solved by the bead stopper 21 of the present invention.

Further, the arrangement of the dummy bead 11 between the suturing beads 10 facilitates the exact discharge of the suturing beads 10, thereby increasing the accuracy of the surgery.

Also, the use of the suturing bead 10 and the suturing needle 20 significantly increases the number of suturing during a single surgery.

Figure 5:
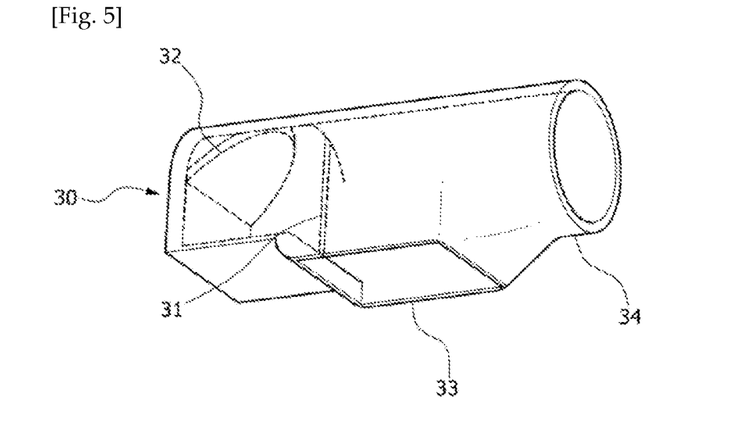
FIG. 5 is a perspective view of a side suction cap according to the present invention.

FIG. 5 is a perspective view of a side suction cap 30 according to the present invention and the side suction cap 30 comprises a coupling part 34 which engages with the end of an endoscope tube 40; a suction port 33 into which the organ is allowed to be introduced perpendicularly to the direction of the engagement of the coupling part with the endoscope tube 40; a push-preventing member 31 which is disposed on the side opposite to the coupling part 34, and is installed the end of the suction port 33 to provide support in such a manner that the organ is not pushed; and a mirror part 32 which is disposed diagonally on the side wall opposite to the coupling part.

The side suction cap 30 is configured to suck the organ near the surgery area in order to prevent other organs or blood vessels from being impaired when the suturing needle 20 penetrates the organ at the surgery area. The coupling part 34 which engages with the endoscope tube 40 is provided on one side and the suction port 33 which sucks the surgery portion is provided on the bottom.

In one embodiment, the endoscope tube 40 directly engages with the coupling part 34 which is formed on the side suction cap 30. Alternatively, the side suction cap 30 may engage with the endoscope tube 40 by means of a connecting tube. Further, sealing means can be added to prevent air-leak at the area where the side suction cap 30 is connected to the endoscope tube 40.

Advantageously, the side suction cap 30 according to the present invention does not damage other organs or blood vessels since it engages with the endoscope tube 40 on the side thereof and the suturing needle 20 is not exposed to the outside unlike the vacuum cap of the prior art.

That is, the suction port 33 of the side suction cap 30 according to the present invention is not formed in the direction that the endoscope tube 40 engages with the side suction cap but formed crossingly to the direction that that the endoscope tube 40 engages with the side suction cap. Therefore, the suction cap 30 removes concerns of damaging other organs or blood vessels outside of the organ. In this case, to prevent the suturing needle 20 from being introduced into the suction port 33, the suction port 33 is preferably perpendicular to the engaging direction of the endoscope tube 40.

Further, there is a possibility that the suturing needle 20 does not penetrate the organ but instead pushes the organ when the suturing needle 20 pricks the organ. To avoid this problem, the side suction cap 30 has a push-preventing member 31 which is disposed on the side opposite to the coupling part 34 and is installed the end of the suction port 33 to provide support in such a manner that the organ is not pushed. The push-preventing member 31 can be arranged vertically as shown in FIG. 5 and alternatively it can be arranged horizontally to watch the organ better.

A mirror part 32 makes it possible to check whether the suturing bead 10 is discharged properly and whether the suturing bead 10 is fixed to the organ properly.

In prior art such as vacuum cap, it is hardly possible to check the organ disposed in the opposite. This problem is solved by the introduction of the mirror part 32.

Figure 6:
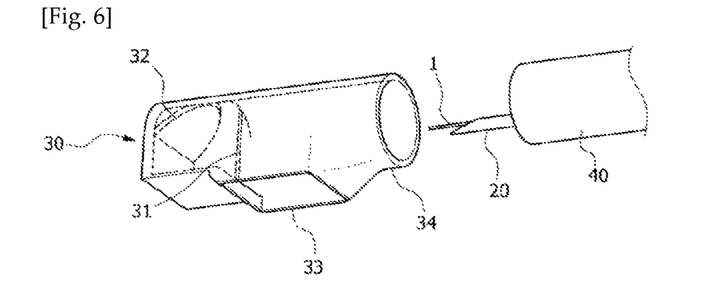
FIG. 6 is an exploded perspective view of an endoscopic organ suturing implement according to the present invention.

FIG. 6 is an exploded perspective view of an endoscopic organ suturing implement according to the present invention.

Referring to FIG. 6, the endoscopic organ suturing implement comprises an endoscope tube 40 which is introduced into the body for a suture surgery and a side suction cap 30 which engages with the end of the endoscope tube 40 to facilitate the surgery area to be suck inside.

The endoscope tube 40 comprises a suturing needle 20 which moves along the length by the operation of the surgeon; a suction tube (not shown) which sucks air inside the side suction cap 30 to form a vacuum inside the side suction cap 30; and a camera (not shown) by which surgeon looks the surgery area. In the suturing needle 20, a bead stopper 21 by which the discharge of the suturing bead 10 is controlled, a plurality of suturing beads 10 and a plurality of dummy beads 11 are arranged in series.

The suturing bead 10 and the dummy bead 11 arranged in the suturing needle 20 can be discharged from the suturing needle 20 by the manipulation of the surgeon. As such, the arrangement to move the suturing needle 20 along the length into and out of the endoscope tube 40 and the arrangement to discharge the suturing bead 10 from the suturing needle 20 are embodied in various forms by the conventional suturing devices, and therefore detailed descriptions for the above arrangements thereof are omitted.

The suturing needle 20 of the endoscopic organ suturing implement according to the present invention is characterized in that it moves only inside the side suction cap 30 to prevent other organs or vessels from being impaired when the needle penetrates the organ at the surgery area.

In the prior art, the suturing needle can impair other organs or vessels since it is exposed out of the vacuum cap. The present invention solved this problem by arranging the push-preventing member 31 inside the side suction cap 30.

It will be appreciated that the spirit of the present invention is illustrated by a description of various examples and various modifications or variations can be made without departing from the scope and spirit of the invention. Therefore, the embodiments disclosed in the present invention are not intended to restrict the spirit of the present invention but intended to describe it, and the scope of the present invention is not limited to the embodiments. The scope of the present invention may be determined by the accompanying claims and may comprise their equivalents.

The invention claimed is:

1. An endoscopic organ suturing implement comprising:
   a suturing bead comprising a body having an arc-shaped cross section and having a length longer than a breadth, and a suture-penetrating part through which a suture passes;
   a suturing needle configured to discharge the suturing bead, the suturing needle being disposed in an endoscope tube;
   a side suction cap comprising a coupling part, and the endoscope tube engaging with the coupling part;
   a suction port opened in the side suction cap, the suction port being formed transverse to a direction of engagement of the coupling part with the side suction cap;
   a push-preventing member disposed on a side of the suction port opposite to the coupling part and the push-preventing member being configured to prevent an organ from being pushed; and
   a mirror disposed diagonally on a side wall of the side suction cap opposite to the coupling part,
   wherein the suturing needle comprises a bead stopper configured to control the discharge of the suturing bead at a discharging opening and a dummy bead of a cylindrical shape and being shorter than the suturing bead and being positioned between the suturing bead and a next suturing bead,
   wherein the suture-penetrating part is constituted of a wire and is inclined along the length of the suturing bead from one side of the body to the other side and protrudes from one side of the body,
   wherein the suture-penetrating part is configured to rotate the suturing bead in a perpendicular direction when the suture is pulled out to fix the body to the organ,
   wherein the dummy bead is discharged after the suturing bead is discharged to check whether the discharged suturing bead is fixed to the organ.

2. The endoscopic organ suturing implement according to claim 1, wherein the suction port is arranged perpendicularly to the direction of the engagement of the endoscope tube with the side suction cap.

3. The endoscopic organ suturing implement according to claim 1, wherein the mirror is configured to check a status of the suturing bead discharged from the suturing needle.

* * * * *